United States Patent [19]

Furutani et al.

[11] Patent Number: 5,084,383
[45] Date of Patent: Jan. 28, 1992

[54] BACILLUS SUBTILIS STRAIN WHOSE EXTRACELLULAR PROTEASE ACTIVITIES ARE REDUCED, METHOD FOR OBTAINING THE STRAIN AND METHOD FOR SECRETING PROTEINS BY USING THE STRAIN

[75] Inventors: Yoshio Furutani, Kanagawa; Masaru Honjo, Mobara; Akira Nakayama, Mobara; Koichi Kawamura, Mobara; Hiroaki Shimada, Mobara; Izumi Mita, Mobara; Akiko Akaoka, Mobara, all of Japan

[73] Assignees: Agency of Industrial Science and Technology; Ministry of International Trade and Industry, both of Tokyo, Japan

[21] Appl. No.: 553,356

[22] Filed: Jul. 18, 1990

Related U.S. Application Data

[63] Continuation of Ser. No. 102,439, Sep. 29, 1987, abandoned.

[30] Foreign Application Priority Data

Oct. 2, 1986 [JP] Japan ................. 61-233285

[51] Int. Cl.$^5$ .............. C12N 15/00; C12N 1/21; C12N 15/75; C12P 21/00
[52] U.S. Cl. ................. 435/69.1; 435/69.4; 435/172.3; 435/252.31; 935/60; 935/74
[58] Field of Search ............ 435/69.1, 69.4, 172.3, 435/252.31; 935/60, 74

[56] References Cited

U.S. PATENT DOCUMENTS

| | | |
|---|---|---|
| 4,711,843 | 12/1987 | Chang . |
| 4,801,537 | 1/1989 | Nagarajan et al. . |
| 4,824,782 | 4/1989 | Furutani et al. .......... 435/172.3 |

FOREIGN PATENT DOCUMENTS

| | | |
|---|---|---|
| 0121352 | 10/1984 | European Pat. Off. . |
| 0133756 | 3/1985 | European Pat. Off. . |
| 0149241 | 7/1985 | European Pat. Off. . |
| 0151760 | 8/1985 | European Pat. Off. . |
| 162291 | 9/1983 | Japan . |
| 59-190 | 4/1984 | Japan . |
| 2171703 | 9/1986 | United Kingdom . |
| 8503949 | 9/1985 | World Int. Prop. O. . |
| 8601825 | 3/1986 | World Int. Prop. O. . |

OTHER PUBLICATIONS

The Operon, edited by Miller & Reznikoff, Cold Spring Harbor Laboratory, 1980, pp. 42–59, 326–328, & 389–392.

Kawamura et al., Construction of a B. subtilis abl. mut. deficientin extracellular alk and neutral proteases, J. Bact. 160:442, 1984.

Yang et al., Cloning of the neutral protease gene of B. subtilis and the use of the cloned gene to create an in vitro derived dele. mutation, J. Bact. 160: 15, 1984.

*Primary Examiner*—Richard A. Schwartz
*Assistant Examiner*—S. L. Nolan
*Attorney, Agent, or Firm*—Fisher, Christen & Sabol

[57] ABSTRACT

Residual extracellular protease activities of a *Bacillus subtilis* strain can be further reduced by introducing a gene for the stimulation of extracellular protease levels into the genomic DNA of the strain.

The resultant strain whose extracellular protease activities are further reduced is transformed with a recombinant plasmid for secretion of a desired protein and the desired protein can be efficiently produced and accumulated in the culture medium in a large amount. The accumulated desired protein can be easily recovered from the culture medium.

For example, the accumulation level of human growth hormone secreted by a *B. subtilis* MT-430 strain carrying recombinant DNA phGH427 for the expression and secretion of human growth hormone can be increased five to tenfold as a result of the above treatment for reduction of the residual extracellular protease activities of the extracellular protease-activity-deficient strain.

6 Claims, 2 Drawing Sheets

Ikeda et al. "Developing of Bacillus subtilis Host-Vector Systems for Protein Production and Secretion Production of Protein A-VIP Fused Protein." *Magazine of the Japan Society for Bioscience, Biotechnology, and Agrochemistry*, vol. 65, No. 03 (Mar. 1991), p. 346. (with translation).

Nakayama et al. "Efficient secretion of the authentic mature human growth hormone by *Bacillus Subtilis*" *Journal of Biotechnology*, vol. 8 (1988), pp. 123–134.

Sloma et al., J. Bacteriol., 170, (1988), pp. 5557–5563.

"Experimental Agricultural Chemistry", pp. 284–285, Asakura Shuppan (1978) with translation.

McLaughlin, et al. "Unique Features in the Ribosome Binding Site Sequence of the Gram-positive *Staphylococcus aureua* β-Lactamase Gene" *The Journal of Biological Chemistry*, vol. 256, (Nov. 10, 1981), pp. 11283–11291.

Schaeffer et al. "Contribution a l'etude génétique de la sporogenèse bactérienne." Comptes Rendus, vol. 251, No. 25 (Dec. 19, 1960) pp. 3125–3127, with translation.

Fuwa, Hidetsuga "A New Method For Microdetermination of Amylase Activity By the Use of Amylose As the Substrate" *The Journal of Biochemistry*, vol. 41, No. 5 (1954), pp. 583–603.

Hagihara et al. "Crystalline Bacterial Proteinase" *The Journal of Biochemistry*, vol. 45, No. 3 (1958), pp. 185–194.

Anagnostopoulos et al. "Requirements For Transformation in *Bacillus subtilis*" *Journal of Bacteriology*, vol. 81 (1961), pp. 741–746.

Marmur, J. "A Procedure for the Isolation of Deoxyribonucleic Acid for Micro-organisms" Journal of Molecular Biology, vol. 3, No. 2 (Apr. 1961), pp. 208–218.

Saito et al. "Preparation of Transforming Deoxyribonucleic Acid by Phenol Treatment" *Biochemica et Biophysica Acta*, vol. 72, No. 4 (Aug. 20, 1963), pp. 619–628.

Mandel et al. "Calcium-dependent Bacteriophage DNA Infection" *Journal of Molecular Biology*, vol. 53 (1970), pp. 159–162.

Uehara et al. "Regulation of Neutral Protease Productivity in *Bacillus subtilis*: Transformation of High Protease Productivity" *Journal of Bacteriology*, vol. 119 (1974), pp. 82–91.

Yamaguchi et al. "Isolation of Mutants Defective in α-Amylase from *Bacillus subtilis*: Genetic Analyses" Journal of Bacteriology, vol. 119, No. 2 (Aug. 1974), pp. 416–424.

Chemical Abstract 84:27437u of Levy et al. "Evidence of homologous relation between thermolysin and neutral protease A of Bacillus subtilis" *Proceedings of the National Academy of Sciences*, vol. 72, No. 11, (1975), pp. 4341–4345.

Blobel et al., "Transfer of Proteins Across Membranes" *The Journal of Cell Biology*, vol. 67, No. 3 (Dec. 1975), pp. 835–851.

*Biochemical Information II*, Boehringer Mannheim, pp. 28–30.

Lehman, I.R. "T4 DNA Polymerase" in: *Method in Enzymology*, vol. 29, (1978), pp. 46–57.

Maxam et al. "A New Method for Sequencing DNA" *Proceedings of the National Academy of Sciences*, vol. 74, No. 2 (Feb. 1977), pp. 560-564.

Gryczan et al. "Characterization of *Staphylococcus aureus* Plasmids Introduced by Transformation into *Bacillus subtilis*, Journal of Bacteriology, vol. 134, No. 1 (Apr. 1978), pp. 318–329.

Bolivar et al. "Plasmids of *Escherichia coli* as Cloning Vectors," in: *Methods in Enzymology* (1979 ed.), vol. 68, pp. 245–267.

Contente et al. "Characterization of Plasmid Transformation in *Bacillus subtilis*: Kinetic Properties and the Effect of DNA Conformation" *Molecular & General Genetics*, vol. 167 (1979), pp. 251–258.

Chang et al. "High Frequency Transformation of *Bacillus subtilis Protoplasts*" *Molecular & General Genetics*, vol. 168 (1979), pp. 111–115.

Gryczan et al. "Molecular Cloning of Heterologous Chromosomal DNA by Recombination between a Plasmid Vector and a Homologous Resident Plasmid in *Bacillus subtilis*," *Molecular & General Genetics*, vol. 177, No. 3 (1980), pp. 459–467.

Takagi, Y. "Experimental Methods for Gene Manipulation", *Kodansha* (1980), p. 139.

Ishikawa et al. "Enzyme Labeling with N,N'-O-Phenylenedimaleimide" in: *Enzyme Immunoassay*, Ishikawa et al. ed. (Tokyo, Igaku-Shoin, 1981), pp. 67–80.

Partial Certified Translation of Otsuka, Eiko, *Kagaku no Ryoiki* (Field of Chemistry).

Tanpakushitsu-Kakusan-Koso, vol. 26, No. 13 (1981) pp. 2043–2046.

Palva et al. "Nucleotide sequence of the promoter and

NH₂-terminal signal peptide region of the α-amylase gene from Bacillus amyloliquefaciens" *Gene*, vol. 15 (1981), pp. 43–51.

Goldfarb et al. "Expression of Tn9-derived chloramphenicol resistance in *Bacillus subtilis*" *Nature*, vol. 293, No. 5830 (Sep. 1981), pp. 309–311.

Williams et al. "Expression of *Excherichia coli* trp genes and the mouse dihydrofolate reductase gene cloned in *Bacillus subtilis*" *Gene*, vol. 16 (1981), pp. 199–206.

Maniatis, T. *Molecular Cloning*, (N.Y., Cold Spring Harbor Laboratory, 1982), pp. 3–5, 51, 52 and 270–274.

Debabov, V. G. "The Industrial Use of Bacilli" in: Dubnau, D. A., ed. *The Molecular Biology of the Bacilli*, vol. 1, (N.Y., Academic Press 1982), pp. 331, 332.

Chang et al. "Expression of Eukaryotic Genes in *B. subtilis* Using Signals of penP" in: Ganesan et al., ed. *Molecular Cloning and Gene Regulation in Bacilli*, (N.Y., Academic Press, 1982), pp. 159–169.

Moran et al. "Nucleotide Sequences that Signal the Initiation of Transcription and Translation in *Bacillus subtilis*" *Molecular & General Genetics*, vol. 186 (1982), pp. 339–446.

Takeichi et al. "Cloning of *Bacillus subtilis* α-Amylase Structural Gene in Plasmid pUB110" *Agricultural and Biological Chemistry*, vol. 47, No. 1 (Jan. 1983), pp. 159–161.

Horinouchi, S. "Expression of Information in Gram-positive Bacteria", *Tanpakushitsu Kakusan-Koso*, vol. 28 (1983), pp. 1468–1478.

Fuji et al. "Molecular Cloning of a Thermostable Neutral Protease Gene from Bacillus stearothermophilus in a Vector Plasmid and Its Expression in *Bacillus stearothermophilus* and *Bacillus subtilis*" *Journal of Bacteriology*, vol. 154, No. 2 (May 1983), pp. 831–837.

Mezes et al. "Construction of penPΔ1, *Bacillus licheniformis* 749/C β-Lactamase Lacking Site for Lipoprotein Modification" *The Journal of Biological Chemistry*, vol. 258, No. 18 (Sep. 25, 1983), pp. 11211–11218.

Tomioka et al. "Abstracts of Papers" *Annual Meeting of the Agricultural Society of Japan*, 1983, p. 33.

Honjo et al. "Cloning and expression of the gene for neutral protease of *Bacillus amyloliquefaciens* in *Bacillus subtilis*" *Journal of Biotechnology*, vol. 1 (1984), pp. 265–277, *Chemical Abstract No.* 103:82709v.

Hayashi et al. "Modification and Processing of *Bacillus Licheniformis Prepenicillinase* in *Escherichia coli*" *The Journal of Biological Chemistry*, vol. 259, No. 16 (Aug. 25, 1984), pp. 10448–10454.

Vasantha et al. "Genes for Alkaline Protease and Neutral Protease from Bacillus Amyloliquefaciens Contain a Large Open Reading Frame Between the Regions Coding for Signal Sequence and Mature Protein" *Journal of Bacteriology*, vol. 159, No. 3 (Sep. 1984), pp. 811–819.

Manabe et al. "N-Terminal Amino Acid Sequences of Neutral Proteases from *Bacillus amyloliquefaciens* and *Bacillus subtilis:* Identification of a Neutral Protease Gene Cloned in *Bacillus subtilis*" *Agricultural and Biological Chemistry*, vol. 49, No. 8 (1985), pp. 2261–2267.

Takagi et al. "Nucleotide Sequence and Promoter Region for the Neutral Protease Gene from *Bacillus stearothermophilus*" *Journal of Bacteriology*, vol. 163, No. 3 (Sep. 1985), pp. 824–931.

Power et al. "Secretion and autoproteolytic maturation of subtilisin" *Proceedings of the National Academy of Science*, vol. 83 (May 1986), pp. 3096–3100.

Schein et al. "Secretion of Mature IFN-α2 and Accumulation of Uncleaved Precursor by Bacillus subtilis Transformed with a Hybrid α-amylase Signal Sequence IFN-α2 Gene" *BIO/TECHNOLOGY*, vol. 4 (Aug. 1986), pp. 721–725.

Honjo et al. "Construction of an Efficient Secretion Host-Vector System In *Bacillus subtilis*" in: Ganesan et al. ed. *Genetics and Biotechnology of Bacilli*, vol. 2 (Academic Press), pp. 364–369.

Ikemura et al. "Requirement of Pro-sequence for the Production of Active Subtilisin E in *Escherichia coli*" *The Journal of Biological Chemistry*, vol. 262, No. 16 (Jun. 5, 1987), pp. 7859–7864.

Takagi et al. "Role of the Pre-Pro-Region of Neutral Protease in Secretion in *Bacillus subtilis*" *Journal of Fermentation and Bioengineering*, vol. 67, No. 2 (1989), pp. 71–76.

Ulmanen, I., et al., (1985), J. Bacteriol., 162, 176–182.

Palva, I., et al., (1983), Gene, 22, 229–235.

Honjo, M., et al., (1985), J. Biotech., 3, 73–84.

Tomioka, N., et al., (1985), J. Biotechnol., 3, 85–96.

Yoneda, Y. and Maruo, B., (1975), J. Bacteriol., 124, 48–54.

Kunst, F., et al., (1974), Biohimie 56, 1481–1489.

Higerd, T., et al. (1972), J. Bacteriol., 112, 1026–1028.

Honjo, M., et al., (1984), J. Biotechnol., 1, 265–277.
Shimada, J., et al., (1985), J. Biotechnol., 2, 75–85.
Birnboim, H. C., and Doly, J., (1979), Nucleic Acids Res., 7, 1513–1523.
David v. Goeddel et al., (1979), Nature, 281, 544.
Saito, Jr., et al., (1961), J. Gen. Appl. Microbial, 7, 243–252.
Yamane, K., et al., (1985), "Molecular Biology of Microbial Differentiation", Hoch, J. A., and Setlow, P. Ecl 117–123, Amer. Soc. for Microbiol.
Honjo, M., et al., (1986), "Bacillus Molecular Genetics and Biotechnology Applns", 2 Ganesan, A., and Hoch, J. A., Ed. Academic Press.
Steinmetz, M., et al., (1976), Mol. Gen. Genet., 148, 281–285.
Schaeffer, P., and Ionesco, H., (1960), Comt. Rerd., 251, 3125.
Laemmli, U.S., (1970), Nature, 277, 680–685.
Millet, J., J. Appl. Bact., 33, (1970), 207–219.
Mantsala et al., J. Bacteriol., 141, (1980), 493 to 501.
Uehara et al., J. Bacteriol, 139, (1979), 583–590.
Hageman, et al., J. Bacteriol., 114, (1973), 612–617.
Stahl, et al., E. J. Bacteriol., 158 (1984), 411–418.
Ehrlich et al., Bacillus Molecular Genetics and Biotechnology Applns. Ganesan, AT and Hoch J. A., ed., Academic Press, (1986), p. 27.
Honjo et al., J. Biotechnol., 6, (1987), 191–204.
Yang et al., J. Bacteriol., 166, (1986), 113–119.
Tanaka et al., J. Bacteriol, 170, (1988), 3593–3600.
Henner et al., J. Bacteriol, 170, (1988), 5102–5109.
Henner et al., Genetics and Biotechnology of Bacilli, Ganesan, AT and Hoch J. A., ed., Academic Press, vol. 2, 1988, p. 3.

```
 1
fMet gly leu gly lys lys leu ser ser ala val ala ala ser phe
GTG  GGT TTA GGT AAG AAA TTG TCT AGT GCT GTA GCC GCT TCC TTT
                                  10 met ser leu thr ile ser leu pro gly val gln ala ala glu asn
ATG AGT TTA ACC ATC AGT CTG CCG GGT GTT CAG GCC GCT GAG AAT
             20                                          30 pro gln leu lys glu asn leu thr asn phe val pro lys his ser
CCT CAG CTT AAA GAA AAC CTG ACG AAT TTT GTA CCG AAG CAT TCT
                             40 leu val gln
TTG GTG CAA
```

BACILLUS SUBTILIS STRAIN WHOSE EXTRACELLULAR PROTEASE ACTIVITIES ARE REDUCED, METHOD FOR OBTAINING THE STRAIN AND METHOD FOR SECRETING PROTEINS BY USING THE STRAIN

This application is a continuation of application Ser. No. 102,439, filed Sept. 29, 1987 now abandoned.

BACKGROUND OF THE INVENTION

1. Field of the Invention

This invention relates to a novel *Bacillus subtilis* strain useful as the host for the highly efficient secretory production of desired proteins by causing the host to secrete the desired proteins using recombinant DNA techniques and to a method for the highly efficient secretory production of the desired proteins by using the strain as the host.

More particularly, this invention relates to a method for producing the desired protein efficiently by utilizing a combination of (a) a novel *B.* subtilis strain as the host obtained by introducing a gene for the stimulation of extracellular protease levels derived from a bacterium of the genus Bacillus into a recipient *B. subtilis* strain whose extracellular protease activities are already reduced so that the extracellular protease activities of the resultant strain become lower than those of the recipient strain; and (b) a recombinant plasmid containing a gene coding for the desired protein joined to an extracellular protease gene or a DNA sequence derived therefrom so as to express the gene and secrete the protein thus expressed.

2. Description of the Prior Art

Recombinant DNA techniques have recently made it possible to cause microorganisms as the host to express foreign genes and therefore desired foreign gene products can be produced by using these techniques.

As the host microorganism, various bacteria including *Escherichia coli*, *B. subtilis* and various yeasts have been generally used.

From the viewpoint of efficient material production, attempts to secrete foreign proteins into the culture media of transformants capable of producing the foreign proteins have been made. As a host microorganism useful for this purpose, the genus Bacillus having the character of secretion of large amounts of extracellular proteins such as protease, amylase and others has been primarily regarded as a suitable host.

Among the genus Bacillus, B. subtilis has in particular attracted attention, not only because it is safe, but also because much information about it has been accumulated in the fields of genetics, biochemistry, molecular biology and applied microbiology. Therefore, efforts have been made to construct hostrecombinant plasmid systems capable of secreting foreign proteins in the culture media by using *B. subtilis* as the host.

In many cases in the attempts in the prior art to cause *B. subtilis* as the host to secrete foreign proteins, the accumulation levels of the secreted proteins were however still low, particularly where the foreign proteins derived from higher eukaryotes. Therefore, the techniques for the secretion of foreign proteins in the prior art are not yet satisfactory in terms of industrial production.

It has been presumed that small accumulation of the secreted proteins may be caused by the degradation of the foreign proteins derived from higher eukaryotes during or after secretion, because, although the mRNAs were synthesized in sufficiently large amounts, the foreign proteins were accumulated only in small amounts (Reference 1).

The *B. subtilis* strain whose extracellular protease activities are reduced to avoid the degradation of the desired protein has been regarded as a suitable host in view of the existing state of the art.

However, no suitable *B. subtilis* strains as the host for the secretion of foreign proteins originating from higher eukaryotes in sufficient amounts are known from various experimental results reported in the prior art.

For example, Palva et al. constructed a *B. subtilis* strain whose extracellular protease activities were reduced, introduced into it a recombinant plasmid containing a combination of an α-amylase signal peptide coding DNA sequence and a human interferon-α gene joined to the downstream side thereof and then obtained transformants. In their experiment on the secretion of human interferon-α by the transformants, the accumulation levels reached $10^5$ units per 1 l of the culture medium. This value corresponds to approximately 1 mg/l-culture medium of human interferon-α, and this level is much lower than that of the α-amylase (Reference 2).

The present inventors attempted the secretory production of human interferon-β by using a *B. subtilis* strain whose extracellular neutral and alkaline protease activities were reduced as the host. In this case, although the strain whose protease activities were reduced was used as the host, the accumulation level (10 mg/l-culture medium) of the secreted human interferon-β was not as high as the present inventors had expected. They also confirmed that the foreign protein produced was rapidly degraded in the absence of a protease inhibitor in the culture medium (Reference 3).

As described above, it has ben difficult in the prior art methods to accumulate the desired foreign proteins derived from higher eukaryotes in large amounts in the culture supernatants only by using as the host *B. subtilis* strains whose extracellular neutral and alkaline protease activities were reduced by the prior art methods.

SUMMARY OF THE INVENTION

The present inventors conducted research in view of the above-described problems and found that, when a gene for the stimulation of extracellular protease levels which was previously isolated by the present inventors (Reference 4) was introduced into a *B. subtilis* strain whose extracellular protease activities were already reduced, halo formation on a casein-agar plate indicating proteolytic activity by the resultant *B. subtilis* strain bearing the gene was controlled in a lower reduced level by the introduction of the gene into the genomic DNA of the recipient train than the level of the control, or the recipient strain itself, contrary to expection.

This invention was thus achieved, based on the new finding of the present inventors.

It is an object of the present invention to provide a novel *B.* subtilis strain whose extracellular protease activities are further reduced and which is useful as the host for the secretory production of a desired protein by using recombinant DNA techniques.

It is another object of the present invention to provide a method for constructing the novel *B. subtilis* strain.

It is still another object of the present invention to provide a method for producing a desired protein efficiently by using the novel *B. subtilis* strain as the host.

The present invention therefore makes it possible to produce the desired protein efficiently by introducing a recombinant plasmid containing a gene coding for the desired protein inserted into a expression-secretion vector having a structure capable of expressing the gene and secreting the protein thus expressed, into a *B. subtilis* strain whose extracellular protease activities are further reduced by the introduction of the gene for the stimulation of extracellular protease levels into its genomic DNA.

As indicated in the Examples that will be given below, the present inventors succeeded in the accumulation of 200 mg of human growth hormone per 1 l of culture medium by using the transformant obtained by introducing a recombinant DNA containing a human growth hormone coding gene following a DNA sequence derived from the promoter and prepro-peptide coding region of an extracellular protease gene, into the *B. subtilis* strain bearing the gene for the stimulation of extracellular protease levels in the genomic DNA.

This accumulation level was five to tenfold greater than in the case of the extracellular neutral and alkaline protease-activity-deficient strains constructed by the prior art methods.

BRIEF DESCRIPTION OF THE DRAWINGS

FIG. 2 shows the nucleotide sequence of the part derived from the extracellular neutral protease prepro-peptide coding region contained in phGH427 and the amino acid sequence corresponding to the nucleotide sequence.

DETAILED DESCRIPTION OF THE INVENTION

Figure 1:
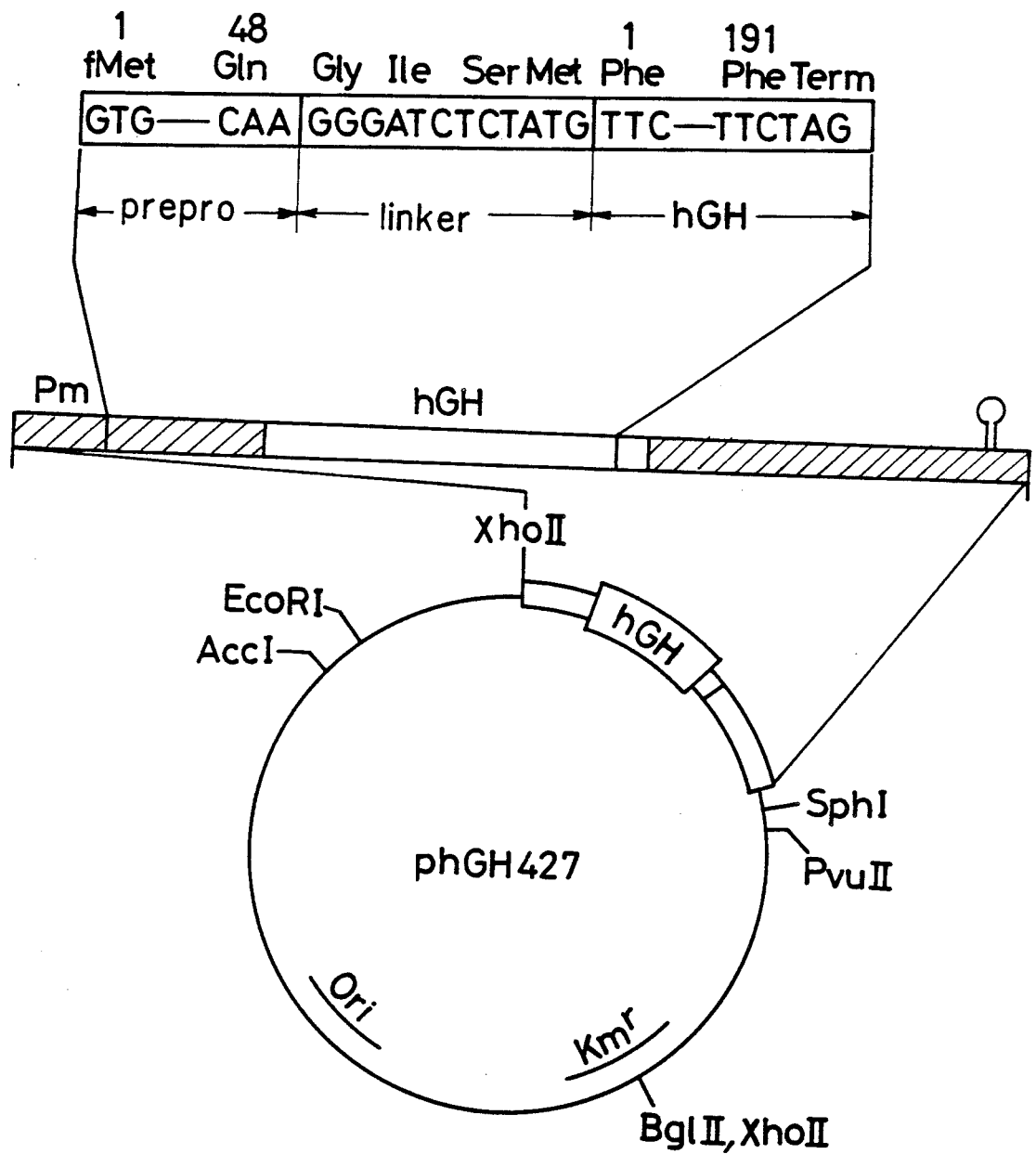
FIG. 1 shows the structure of plasmid phGH427. In this drawing, the slanting lines represent the part derived from extracellular neutral protease gene. Pm, prepro and hGH represent the promoter region, the prepro-peptide coding region and the DNA fragment containing the mature human growth hormone coding gene, respectively.

As the gene for the stimulation of extracellular protease levels, pap (Reference 5), sacQ (Reference 6), hpr (Reference 7) and other genes are known from genetic analysis.

As the gene for the stimulation of extracellular protease levels, any gene which has the effect of controlling halo formation on a casein-agar plate in an extracellular protease-activity-deficient *B. subtilis* strain in a further reduced level by the introduction of the gene into the genomic DNA of the strain can be used in the present invention.

The gene for the reduction of the residual extracellular protease activities of the strain as the recipient of the gene can also be either one that is already known or one that is newly isolated by recombinant DNA techniques.

In order to easily carry out the present invention, genes isolated by recombinant DNA techniques are preferable, because they are easily available.

Among them, a DNA fragment containing the DNA sequence which was previously isolated from *B. amyloliquefaciens* by the present inventors (Reference 8) and one of whose strands comprises the following nucleotide sequence is useful:

| | | | |
|---|---|---|---|
| GTGTCACGCA | GATACTTTTA | CACATACTTT | TCGGTGAAAA |
| ATCCCGCAAA | AACGTTTACA | CTATTAGTAA | CAGATCAAAT |
| ACCTAGGACT | CGTTCACCAT | ACACAATTCA | TTGATCTTTC |
| AAAAAAAGGA | GTGTGGAAAC | GGTGGAAAAG | AAATTAGAAG |
| AAGTAAAGCA | ATTATTATTC | CGACTTGAAA | ATGATATCAG |
| AGAAACAACC | GACTCATTAC | GAAACATTAA | CAAAAGCATT |
| GATCAGCTCG | ATAAATTCTC | ATATGCAATG | AAAATTTCTT |
| AAAAAGACTT | GGAAACAAGT | CTTTTTTTTG | TGCATTTTTC |
| ACCCATTTCA | TGGATAAAGT | ATTATACGAT | |

In order to obtain the *B. subtillis* strain of the present invention by introducing the gene for the stimulation of extracellular protease levels into the genomic DNA, genetic recombination based on the DNA sequence homology between the genomic DNA of the recipient *B. subtilis* strain and the gene introduced can be used. Any other methods by which the gene can be introduced into the genomic DNA of the recipient strain can also be employed.

The *B. subtilis* strain whose extracellular neutral and-/or alkaline protease activities are reduced as the recipient of the gene for the stimulation of extracellular protease levels can be obtained by processes utilizing mutagenesis or genetic recombination. For mutagenesis, contact with, for example, mutagens, ultraviolet or gamma irradiation can be used.

For gentic recombination, a method which comprises the steps of isolating an extracellular protease gene from a *B. subtilis* strain, subjecting the isolated gene to deletion in vitro and returning the gene having deletion to the original strain can be employed. Processes utilizing mutagenesis and genetic recombination can be combined if required.

However, processes utilizing genetic recombination are preferable, because the pertinent deletion can be easily caused in the extracellular protease gene.

The present inventors newly found, as the basis of the present invention, that the residual extracellular protease activities of the recipient strain obtained by the above-described manner can be still more surprisingly reduced by introducing a plasmid containing the gene for the stimulation of extracellular protease levels into the recipient or by inserting the gene into the genomic DNA of the recipient so that the gene is retained in the genomic DNA of the recipient.

The production of the desired foreign protein according to this invention utilizing a secretion process can be carried out by introducing a recombinant DNA for secretion of the desired protein into the *B. subtilis* strain bearing the above gene for the stimulation of extracellular protease levels in its genomic DNA as the host and culturing the transformants thus obtained.

The recombinant plasmid for the secretion of the desired protein used for this purpose can include any plasmid that is capable of secreting the desired protein. The recombinant plasmid can be constructed by joining a gene coding for the desired protein or a DNA fragment containing it to the downstream side of a region necessary for the expression of the gene and the secretion of the desired protein. As the region necessary for the expression and the secretion, a region derived from the promoter and the prepro-peptide coding region, both of which are derived from extracellular protease gene of a bacterium of the genus Bacillus, can be used.

For example, as the useful recombinant DNA, pPIF25 for the secretion of human interferon-β (Reference 9) and other recombinant plasmids were already constructed by the present inventors.

Any extracellular protease gene of a bacterium of the genus Bacillus can be used as a material for the recombinant DNA to construct the region involved in the gene expression and the protein secretion.

Extracellular protease genes for the construction of the recombinant plasmid include, for example, extracellular neutral and alkaline protease genes derived from *B. amyloliquefaciens*; extracellular neutral and alkaline protease genes derived from *B. subtilis*; and extracellular neutral and alkaline protease genes derived from *B. licheniformis*.

The recombinant DNA for the expression and the secretion can be introduced into the host strain carrying the gene for the stimulation of extracellular protease levels in its genomic DNA by any conventional method for transformation including, for example, protoplast transformation.

The desired protein can be produced by cultivating the transformant obtained by the method described above in a liquid culture medium. For this cultivation, any conventional culturing method can be employed.

The desired protein can be prepared from the culture medium by any conventional method used for the recovery and purification of proteins.

As described above, the present invention makes it possible to cause a host *B. subtilis* strain to produce a foreign protein originating from a higher eukaryote in a large amount which could not be realized in the prior art methods. Moreover, the desired protein accumulated in a large amount in the culture medium can be easily recovered and purified.

The present invention is more specifically explained in the following examples. However, these examples are not to be construed to limit the scope of the present invention.

EXAMPLE 1

Construction of a *B. subtilis* strain carrying a gene for the stimulation of extracellular protease levels in its genomic DNA

*B. subtilis* MT-400(FERM BP-1078) strain was used in this example. This strain is a genetically engineered extracellular neutral and alkaline protease-deficient strain and its extracellular protease activities correspond to 5% or less of those of the wild type strain on the extracellular protease activities.

A gene for the stimulation of extracellular protease levels was introduced into the *B. subtilis* MT-400 strain according to the following procedure:

First, plasmid pNP181 (Reference 10) in which a gene for the stimulation of extracellular protease levels was cloned was prepared from *B. subtilis* MT-0181(FERM BP-343) strain bearing the plasmid pNP181 by the method of Gryczan et al. For this preparation, *B. subtilis* MT-0181 cells grown in 1 l of LB-medium at 30° C. for 12 hours were used. The restriction endonuclease cleavage sites of the plasmid thus obtained were analyzed by treating the plasmid with various restriction endonucleases. Thus, the prepared plasmid was identified as pNP181.

Separately, a competent culture of the *B. subtilis* MT-400 strain was prepared according to the method of Saito et al(Reference 17). Then, 0.5 μg of plasmid pNP181 was added to the competent culture (500 μl) and the mixture was incubated at 37° C. for 1 hour.

After the incubation, the whole culture (500 μl) was added to 20 ml of Schaeffer sporulation medium (Reference 11) supplemented with 5 μg/ml of kanamycin and then the incubation was continued at 37° C. for 24 hours.

Then, 1.5 ml portion of the culture was withdrawn as a sample and heated at 70° C. for 10 minutes. After the heat treatment, the culture was diluted $10^4$-, $10^5$- and $10^6$-fold with saline and then 100 μl of each diluted solution was transferred onto TBAB plates (product of Difco).

The inoculated plates were incubated at 37° C. overnight and then the colonies grown on the plates were transferred both onto fresh TBAB plates and onto fresh TBAB plates containing 5 μg/l to test kanamycin resistance. The inoculated plates were further incubated at 37° C. for 15 hours.

After completion of the incubation, 200 colonies grown on the TBAB plates but not on the TBAB-kanamycin plates were selected and then transferred onto casein-agar plates (Reference 12). The plates were incubated at 37° C. for 60 hours to test extracellular protease activities.

After the 60 hours' incubation, the halo formation around each colony grown on the plates was observed. Except for one colony, 199 colonies formed clear halos around them. The colony which did not form a halo was designated as the *B. subtilis* MT-430(FERM BP-1079) strain.

When the *B. subtilis* MT-430 strain was cultivated in a Penassay broth (product of Difco), cells in the logarithmic growth phase were observed to be long filamentous. This morphological change is peculiar to the *B. subtilis* cells transformed with the plasmid pNP181.

Separately, the loss of the plasmid in the MT-430 strain was confirmed by the alkaline plasmid preparation method (Reference 14).

Since the *B. subtilis* MT-400 strain bearing pNP181 did not form a halo on the casein plate and exhibited the above morphological change similar to the MT-430 strain and since the MT-430 strain bore no plasmid, the MT-430 strain was considered to retain the gene for the stimulation of extracellular protease levels derived from plasmid pNP181 in its genomic DNA.

Further, the present inventors confirmed that the genomic DNA of the MT-430 strain could transform a *B. subtilis* wild-type strain on extracellular protease activities into a protease-overproductive strain.

Thus, it was concluded from this genetic analysis that the gene for the stimulation of extracellular protease levels existed in the genomic DNA of the *B. subtilis* MT-430 strain.

EXAMPLE 2

Introduction of a recombinant DNA containing a combination of extracellular protease gene and human growth hormone gene into the *B. subtilis* MT-430 strain As a recombinant DNA for the secretion of human growth hormone, plasmid phGH427 (FIG. 1) was used. This plasmid contained a first DNA fragment comprising the promoter, the pre-peptide coding region and a portion of the pro-peptide coding region (composed of 63 nucleotides coding for 21 amino acids), all of which are derived from neutral protease gene of *B. amyloliquefaciens*; and a second DNA fragment joined to the downstream side of the first DNA fragment which comprised a DNA sequence coding for the mature human growth hormone.

The plasmid phGH427 was constructed by the process including the steps of treating plasmid pNP150 (constructed previously by the present inventors: Reference 13), in which *B. amyloliquefaciens* neutral protease gene was cloned, with exonuclease Bal 31 to hydrolyzing the plasmid from the cleavage site for restriction endonuclease Pvu I located in the prepro-peptide coding region of the neutral protease gene and joining the resulting DNA fragment to a DNA fragment comprising the gene coding for the mature human growth hormone through a linker.

The plasmid pNP150 used in the above procedure was prepared from *B. subtilis* MT-0150 (FERM BP-425) by the conventional method, and the DNA fragment comprising human growth hormone gene was chemically synthesized based on the publicly known nucleotide sequence coding for the mature human growth hormone (Reference 16).

The *B. subtilis* MT-430 strain was transformed with the plasmid phGH427 by protoplast transformation. Then, 50 colonies were selected from the resulting kanamycin-resistant transformants.

Cells of each selected colony were suspended in LB-medium, and the resulting suspension was incubated with shaking at 30° C. for 15 hours.

After completion of the incubation, the supernatant of each culture was recovered and the accumulation of human growth hormone in the culture supernatants were assayed by enzyme immunoassay and detected by the double immunodiffusion test. It was shown that all of the selected colonies were capable of secreting human growth hormone.

One of the resulting transformants capable of secreting human growth hormone was designated as *B. subtilis* MT-430(phGH427)(FERM BP-1080) and the secretory production of human growth hormone by using this strain was tested in the following example.

EXAMPLE 3

Secretory production of human growth hormone by using the *B. subtilis* MT-430(phGH427) strain as the host The *B. subtilis* MT-430 (phGH427) strain and the *B. subtilis* MT-400 (phGH427) strain as a control obtained by transforming the *B. subtilis* MT-400(FERM BP-1078) strain with plasmid phGH427 by the method described in Example 2 were separately cultured with shaking in 100 ml of LB-medium at 30° C. for 17 hours.

After completion of the shaking culture, cells were collected by centrifugation and suspended in a fresh twofold concentrated LB-medium. Then shaking culture was continued at 30° C.

After 8 hours, the cell densities (A660) of the two cultures reached 9.86 and 10.00, respectively, and the pHs of their culture supernatants were 8.06 and 7.98, respectively.

Then, the accumulation of human growth hormone in their culture supernatants was assayed by enzyme immunoassay and detected by double immunodiffusion test. The results of the enzyme immunoassay showed that the MT-430 (phGH427) strain accumulated 205 mg/l-culture medium of human growth hormone, while the MT-400 (phGH427) strain accumulated 30 mg/l-culture medium of human growth hormone.

In the double immunodiffusion test, human growth hormone secreted by the two transformants was indistinguishable from that derived from human pituitary.

The *B. subtilis* MT-430 (phGH427) strain was cultivated at 30° C. for 17 hours and a culture supernatant was prepared. Then, trichloroacetic acid was added to 100 μl of the culture supernatant to obtain a precipitate.

The resulting precipitate was collected and further dissolved in a sample buffer solution and subjected to SDS polyacrylamide gel electrophoresis according to Laemmli (Reference 15). The result showed that 20–30% of the precipitate was human growth hormone.

As described in the above examples, it is clear that the present invention makes it possible to produce a foreign protein efficiently in a large amount in a host-recombinant plasmid system comprising a combination of the *B. subtilis* MT-430 strain as the host and a recombinant plasmid for the secretion of the foreign desired protein containing the region involved in the gene expression and the protein secretion which is derived from an extracellular neutral protease gene of a bacterium of the genus Bacillus. The accumulation level of the secreted protein, which could not be achieved in the prior art by using *B. subtilis*, can be obtained by the present invention.

List of References

1. Ulmanen, I. (1985) J. Bacteriol., 162 176–182, Yamane, K. et al. (1985) in "Molecular Biology of Microbial Differentiation" Hoch, J. A., and Setlow, P. Ecl 117–123, American Soc. for Microbiol.
2. Palva, I. et al. (1983) Gene, 22 229–235.
3. Honjo, M. et al. (1985) J. Biotech., 3 73–84; Honjo, M. et al. (1986) In "Genetics and Biotechnology of Bacilli" 2 Ganesan, A., and Hoch, J. A. Ed Academic Press.
4. Tomioka, N. et al. (1985) J. Biotechnol., 3 85–96.
5. Steinmety, M. et al. (1976) Mol. Gen. Genet., 148 281–285, Yoneda, Y.; and Maruo, B. (1975) J. Bacteriol., 124 48–54.
6. Kunst. F. et al. (1974) Biochimie 56 1481–1847.
7. Higerd, T. et al. (1972) J. Bacteriol., 112 1026–1028.
8. Tomioka, N. et al. (1985) J. Biotechnol., 3 85–96.
9. Honjo, M. et al. (1985) J. Biotechnol., 3 73–84.
10. Tomioka, N. et al. (1985) J. Biotechnol., 3 85–96.
11. Schaeffer, P. and Ionesco, H. (1960) Comt. Rerd., 251 3125.
12. Honjo, M. et al. (1985) J. Biotechnol., 1 73–84.
13. Honjo, M. et al. (1984) J. Biotechnol., 1 265–277; Shimada, H. et al. (1985) J. Biotechnol., 2 75–85.

14. Birnboim, H. C. and Doly, J. (1979) Nucleic Acids Res., 7 1513-1523.
15. Laemmli, U. K. (1970) Nature, 277 680-685.
16. David V. Goeddel et al. (1979) Nature, 281 544.
7. Saito, H. et al. (1961) J. Gen. Appl. Microbial, 7 243-252.

The strains under the deposit FERM BP number given in the parentheses used in the above-described examples are deposited in the Fermentation Research Institute of the Agency of Industrial Science and Technology, 1-3, Higashi 1 chome, Yatabe-machi, Tsukuba-gun, Ibaraki-ken, 305 Japan under the Budapest Treaty.

What is claimed is:

1. An extracellular protease-activity-deficient *Bacillus subtilis* strain which is obtained by introducing a gene comprising Sac Q (BamF) into the genomic DNA of an extracellular alkaline- and neutral-protease-deficient-*B.subtilis* recipient to further reduce residual extracellular protease activity of said recipient, said gene involved in the regulation of extracellular protease genes comprising the following nucleotide sequence:

GTGTCACGCA GATACTTTTA CACATACTTT

TCGGTGAAAA ATCCCGCAAA AACGTTTACA

CTATTAGTAA CAGATCAAAT ACCTAGGACT

CGTTCACCAT ACACAATTCA TTGATCTTTC

AAAAAAGGA GTGTGGAAAC GGTGGAAAAG

AAATTAGAAG AAGTAAAGCA ATTATTATTC

CGACTTGAAA ATGATATCAG AGAAACAACC

GACTCATTAC GAAACATTAA CAAAAGCATT

GATCAGCTCG ATAAATTCTC ATATGCAATG

AAAATTTCTT AAAAAGACTT GGAAACAAGT

CTTTTTTTTG TGCATTTTTC ACCCATTTCA

TGGATAAAGT ATTATACGAT;

wherein said recipient is FERM-BP 1078.

2. A method for producing desired protein comprising the steps of:
   (a) operably linking, 5' to 3', a promoter, a sequencer coding for a peptide for secretion and a gene coding for the desired protein in a plasmid replicable in *B. subtilis* to obtain a recombinant plasmid, whereby expression and secretion of the desired protein in *B. subtilis* is directed by the promoter and the sequence coding for a peptide for secretion;
   (b) introducing the recombinant plasmid into *B. subtilis* strain of claim 1 to obtain a transformant;
   (c) culturing the transformant in a culture medium to obtain the desired protein secreted in the culture medium.

3. A method as claimed in claim 2, wherein the promoter and the sequence coding for a peptide for secretion are of an extracellular protease gene of a bacterium of the genus Bacillus.

4. A method as claimed in claim 3 wherein the extracellular protease gene used for the construction of the recombinant plasmid is an extracellular neutral protease gene.

5. A method as claimed in anyone of claims 2, 3 or 4, wherein the desired protein is human growth hormone.

6. *B. subtilis* strain FERM BP-1080 carrying recombinant plasmid phHG 427 for the secretion of human growth hormone.

* * * * *

UNITED STATES PATENT AND TRADEMARK OFFICE
CERTIFICATE OF CORRECTION

PATENT NO. : 5,084,383

DATED : January 28, 1992

INVENTOR(S) : Furutani et al.

It is certified that error appears in the above-identified patent and that said Letters Patent is hereby corrected as shown below:

On the Title Page, Item [73] Assignee:

The words --extra-ministerial bureau of-- are inserted before "Ministry".

The words "both of" are deleted.

Signed and Sealed this

First Day of March, 1994

Attest:

BRUCE LEHMAN

Attesting Officer

Commissioner of Patents and Trademarks